United States Patent
Liakat et al.

(10) Patent No.: US 10,441,201 B2
(45) Date of Patent: Oct. 15, 2019

(54) NONINVASIVE MID-INFRARED IN VIVO GLUCOSE SENSOR

(71) Applicants: Sabbir Liakat, Princeton, NJ (US); Claire F. Gmachl, Princeton, NJ (US); Anna P. M. Michel, Woods Hole, MA (US); Kevin Bors, Maple Glen, PA (US)

(72) Inventors: Sabbir Liakat, Princeton, NJ (US); Claire F. Gmachl, Princeton, NJ (US); Anna P. M. Michel, Woods Hole, MA (US); Kevin Bors, Maple Glen, PA (US)

(73) Assignee: THE TRUSTEES OF PRINCETON UNIVERISITY, Princeton, NJ (US)

( * ) Notice: Subject to any disclaimer, the term of this patent is extended or adjusted under 35 U.S.C. 154(b) by 508 days.

(21) Appl. No.: 14/470,386

(22) Filed: Aug. 27, 2014

(65) Prior Publication Data
US 2015/0065823 A1 Mar. 5, 2015

Related U.S. Application Data

(60) Provisional application No. 61/982,577, filed on Apr. 22, 2014, provisional application No. 61/870,529, filed on Aug. 27, 2013.

(51) Int. Cl.
*A61B 5/1455* (2006.01)
*A61B 5/145* (2006.01)
*A61B 5/1495* (2006.01)

(52) U.S. Cl.
CPC ........ *A61B 5/14532* (2013.01); *A61B 5/1455* (2013.01); *A61B 5/1495* (2013.01)

(58) Field of Classification Search
None
See application file for complete search history.

(56) References Cited

U.S. PATENT DOCUMENTS 5,267,152 A * 11/1993 Yang .................... A61B 5/1455
250/339.09
6,484,044 B1 * 11/2002 Lilienfeld-Toal .... A61B 5/0095
600/310
(Continued)

OTHER PUBLICATIONS

William L. Clarke et al., "Evaluating Clinical Accuracy of Systems for Self-Monitoring of Blood Glucose", Technical Articles, 10, 622-628, Sep.-Oct. 1987.
(Continued)

*Primary Examiner* — Eric F Winakur
*Assistant Examiner* — Marjan Fardanesh
(74) *Attorney, Agent, or Firm* — Meagher Emanuel Laks Goldberg & Liao, LLP

(57) ABSTRACT

A noninvasive mid-infrared in vivo glucose sensor for use in connection with the skin of a test subject is disclosed. The sensor includes a mid-infrared light source configured to deliver a light beam to the skin of the test subject, a collector element configured to collect backscattered light from the skin and direct it to the detector, and a detector element configured to measure the collected backscattered light from the skin. The mid-infrared light source may be a quantum cascade laser. The sensor may include optical fibers configured to deliver the light beam to the skin of the test subject. The collector element may be an integrating sphere or a bundle of two or more optical fibers. The sensor may also include a probe containing or connecting to optical fibers coupled to the mid-infrared light source and configured to be placed on the skin to take glucose level readings.

11 Claims, 3 Drawing Sheets

(56) References Cited

U.S. PATENT DOCUMENTS

| | | | |
|---|---|---|---|
| 2009/0021724 A1* | 1/2009 | Mahadevan-Jansen | A61B 5/0066 356/73 |
| 2009/0105564 A1* | 4/2009 | Tokita | A61B 5/14532 600/310 |
| 2010/0010325 A1* | 1/2010 | Ridder | A61B 5/0075 600/310 |
| 2010/0261995 A1* | 10/2010 | McKenna | A61B 5/06 600/424 |

OTHER PUBLICATIONS

David M. Haaland and Edward V. Thomas, "Partial Least-Squares Methods for Spectral Analyses. 1. Relation to Other Quantitative Calibration Methods and the Extraction of Qualitative Information", Anal. Chem., 60, 1193-1202, 1988.

Hristison, H. A. Mackenzie, "Laser Photoacoustic Determination of Physiological Glucose Concentrations in Human Whole Blood", Medical and Biological Engineering and Computing, 31, 284-290, 1993.

Sijmen De Jong, "SIMPLS: An Alternative Approach to Partial Least Squares Regression", Chemometrics and Intelligent Laboratory Systems, 18, 251-263, 1993.

Omar S. Khalil, "Spectroscopic and Clinical Aspects of Noninvasive Glucose Measurements", Clinical Chemistry, 45, 165-177, 1999.

Michael E. Lamar, Thomas J. Kuehl et al., "Jelly beans as an alternative to a fifty-gram glucose beverage for gestational diabetes screening", Am. J. Obstet. Gynecol., 181, 1154-1157, 1999.

Suresh N. Thennadil, Jessica L. Rennert et al., "Comparison of Glucose Concentration in Interstitial Fluid, and Capillary and Venous Blood During Rapid Changes in Blood Glucose Levels", Diabetes Technology & Therapeutics, 3, 357-365, 2001.

Katsuhiko Maruo, Mitsuhiro Tsurugi et al., "In Vivo Noninvasive Measurement of Blood Glucose by Near-Infrared Diffuse-Reflectance Spectroscopy", Applied Spectroscopy, 57, 1236-1244, 2003.

W. Blake Martin, Sergey Mirov et al., "Middle Infrared, Quantum Cascade Laser Optoelectronic Absorption System for Monitoring Glucose in Serum", Applied Spectroscopy, 59, 881-884, 2005.

Hermann Von Lilienfeld-Toal, Michael Weidenmuller et al., "A novel approach to non-invasive glucose measurement by mid-infrared spectroscopy: the combination of quantum cascade lasers (QCL) and photoacoustic detection",Vibrational Spectroscopy, 38, 209-215, 2005.

Katsuhiko Maruo, Tomohiro Oota, Mitsuidr.O Tsurugi et al., "New Methodology to Obtain a Calibration Model for Noninvasive Near-Infrared Blood Glucose Monitoring", Applied Spectroscopy, 60, 441-449, 2006.

Markus Brandstetter, Andreas Genner et al., "Tunable external cavity quantum cascade laser for the simultaneous determination of glucose and lactate in aqueous phase", The Royal Society of Chemistry, 135, 3260-3265, 2010.

Narahara Chari Dingari, Ishan Barnan et al., "Investigation of the specificity of Raman spectroscopy in non-invasive blood glucose measurements", Anal. Bioanal. Chem., 400, 2871-2880, 2011.

X. Guo, A. Mandelis, B. Zinman, "Non-invasive Glucose Measurements Using Wavelength Modulated Differential Photothermal Radiometry", Int. J. Thermophys., 2012.

Koushik Chowdhury, Anuj Srivastava et al., "Challenges & Countermeasures in Optical Noninvasive Blood Glucose Detection", International Journal of Innovative Research in Science, Engineering and Technology, 2, 329-334, Jan. 2013.

A. N. Bashkatov, A Genina et al., "Optical properties of human skin, subcutaneous and mucous tissues in the wavelength range from 400 to 2000nm", J. Phys. D: Appl. Phys., 38, 2543-2555, 2005.

Rohit Bhargava, "Infrared Spectroscopic Imaging: The Next Generation", Applied Spectroscopy, 1091-1120, Jul. 2012.

Nikiforos Kollias and Georgios N. Stamatas, "Optical Non-Invasive Approaches to Diagnosis of Skin Diseases", Optical Diagnostics in Dermatology, 7, 64-75, Dec. 2002.

Rong Kong and Rohit Bhargava, "Characterization of porcine skin as a model for human skin studies using infrared spectroscopic imaging", Analyst, 136, 2359-2366, 2011.

Aravind Krishnaswamy and Gladimir V.G. Baranoski, "A Biophysically-Based Spectral Model of Light Interaction with Human Skin", Eurographics, 23, 331-340, 2004.

Richard Mendelsohn, Carol R. Flach, David J. Moore, "Determination of molecular conformation and permeation in skin via IR spectroscopy, microscopy, and imaging", Biochimica et Biophysica Acta, 1758, 923-933, 2006.

Judith R. Mourant, James P. Freyer, Andreas H. et al., "Mechanisms of light scattering from biological cells relevant to noninvasive optical-tissue diagnostics", Applied Optics, 37, 3586-3593, Jun. 1998.

Iyad S. Saidi, Steven L. Jacques, and Frank K. Tittel, "Mie and Rayleigh modeling of visible-light scattering in neonatal skin", Applied Optics, 34, 7410-7418, Nov. 1995.

Joseph M. Schmitt and Gitesh Kumar, "Optical scattering properties of soft tissue: a discrete particle model", Applied Optics, vol. 37, 2788-2798, May 1998.

Alfred Vogel, and Vasan Venugopalan, "Mechanisms of Pulsed Laser Ablation of Biological Tissues", Chem. Rev., 103, 577-644, 2003.

Liqun Wang and Boris Mizaikoff, "Application of multivariate data-analysis techniques to biomedical diagnostics based on mid-infrared spectroscopy", Anal Bioanal Chem., 391, 1641-1654, 2008.

S. Liakat, A. Michel, K. Bors, and C. Gmachl, "Mid infrared ($\lambda$=8.4-9.9 µm) light scattering from porcine tissue," Appl. Phys. Lett, 101, 093705 (2012).

A. Michel, S. Liakat, K. Bors, and C. Gmachl, "In vivo measurement of mid-infrared light scattering from human skin," Biomed. Opt. Express, 4(4), 520-530 (2013).

S. Liakat, K. Bors, T. Huang, A. Michel, E. Zanghi, and C. Gmachl, "In vitro measurements of physiological glucose concentrations in biological fluids using mid-infrared light," Biomed. Opt. Express, 4(7), 1083-1090 (2013).

S. Liakat, K. Bors, T. Huang, A. Michel, E. Zanghi, and C. Gmachl, "In vitro measurements of physiological glucose concentrations in biological fluids using mid-infrared spectroscopy," CLEO: Science and Innovations, Jun. 9-14, 2013, San Jose, CA, USA.

S. Liakat, K. Bors, T. Huang, A. Michel, E. Zanghi, and C. Gmachl, "Use of partial least squares regression analysis to predict physiological glucose concentrations in vitro," Imaging Congress: Fourier Transform Spectroscopy (FTS), Jun. 23-24, 2013, Arlington, VA, USA.

S. Liakat, Z. Yu, T. Huang, L. Xu, and C. Gmachl, "Progress towards noninvasive in vivo glucose sensing in the mid-IR", Submitted abstract to ITQW 2013, to be held in Sep. 2013 in Lake George, NY, USA.

Robin P. Smith, Samantha J. Riesenfeld, et al., "A compact, in vivo screen of all 6-mers reveals drivers of tissue-specific expression and guides synthetic regulatory element design", Genome Biology, 14, 2013.

Miguel A. Pleitez, Tobias Lieblein, et al., "In Vivo Noninvasive Monitoring of Glucose Concentration in Human Epidermis by Mid-Infrared Pulsed Photoacoustic Spectroscopy", Analytical Chemistry, 85, 1013-1020, 2012.

Jin Liu, Rong Liu, Kexin Xu, "The Accuracy of Noninvasive Glucose Sensing Based on Near-Infrared Spectroscopy", 2013.

T. Greve et al., "Disease quantification in dermatology: in vivo near-infrared spectroscopy measures correlate strongly with the clinical assessment of psoriasis severity", Journal of Biomedical Optics, 18, 2013.

J. Hun et al., "Effect of Thermal Damage and Biaxial Loading on the Optical Properties of a Collagenous Tissue", Transactions of the ASME, 125, 540-548, 2003.

J. Li et al., "Quantum Cascade Laser Spectrometry Techniques: A New Trend in Atmospheric Chemistry", Applied Spectroscopy Reviews, 48, 523-559, 2013.

(56) References Cited

OTHER PUBLICATIONS

A. Seddon, "Mid-infrared (IR)—A hot topic: The potential for using mid-IR light for non-invasive early detection of skin cancer in vivo", Phy. Status Solodi., 250, 1020-1027, 2013.

H. Ullah et al., "Quantification of Glucose Levels in Flowing Blood Using M-Mode Swept Source Optical Coherence Tomography", Laser Methods in Chemistry, Biology and Medicine, 22, 797-804, 2012.

"Handbook of Optical Sensing of Glucose in Biological Fluids and Tissues (Series in Medical Physics and Biomedical Engineering)" Ch. 1-5, CRC Press, Boca Raton, 2009.

\* cited by examiner

NONINVASIVE MID-INFRARED IN VIVO GLUCOSE SENSOR

CROSS-REFERENCE TO PRIOR FILED APPLICATIONS

This application claims the benefit of U.S. Provisional Application No. 61/870,529, filed Aug. 27, 2013, and 61/982,577, filed Apr. 22, 2014, both of which are incorporated herein in their entirety.

TECHNICAL FIELD

The present disclosure generally relates to glucose sensors and more particularly noninvasive glucose sensors incorporating midrange-infrared light sources with relatively high peak power and low average power to obtain more robust signals from skin regions where mid-IR light had previously been considered to be undetectable.

BACKGROUND OF THE INVENTION

Diabetes is a disease that over 340 million people worldwide live with. Daily blood glucose monitoring is essential to management of the disease, as it impacts diet and required medication. Currently, the most accurate method of monitoring involves an often painful finger prick and the drawing of blood. The development of a non-invasive in vivo glucose concentration monitor would make this routine daily practice much more convenient for diabetics.

Methods of noninvasive in vivo glucose detection have been studied for decades but traditional invasive monitors still remain the standard. Prior optical noninvasive in vivo glucose detection studies have been focused on the near-infrared (near-IR) due to the presence of resonant glucose overtone and combination bands combined with low water absorption in that region, which allows for greater penetration of light into skin. However, absorption features of other biological absorbers such as hemoglobin and amides are also relatively broad and strong in the near-IR, leading to the necessity of complex multivariate analysis to extract the impact of only glucose on the spectrum obtained from backscattered light. The unpredictability of concentrations of these other absorbers leads to chance temporal correlations and the need to calibrate data using complex sets recorded over multiple days. Work using Raman spectroscopy with near-IR light has also been reported, but the method has its own obstacles to overcome, such as the relatively weak signal associated with Raman scattering. A non-invasive in-vivo glucose sensor that does not utilize near-IR light is therefore desirable.

BRIEF SUMMARY OF THE INVENTION

A noninvasive mid-infrared in vivo glucose sensor for use in connection with the skin of a test subject is disclosed. The sensor includes a mid-infrared light source configured to deliver a light beam to the skin of the test subject, a collector element configured to collect backscattered light from the skin and direct it to the detector, and a detector element configured to measure the collected backscattered light from the skin. The mid-infrared light source may be a quantum cascade laser. The sensor may include optical fibers configured to deliver the light beam to the skin of the test subject. The optical fibers may be hollow core optical fibers. The collector element may be an integrating sphere. The collector element may be a bundle of two or more optical fibers.

The sensor may also include a probe containing or connecting to optical fibers coupled to the mid-infrared light source. The probe may be configured to be placed on the skin of the test subject to take glucose level readings. The mid-infrared light source may be tuned to between around 1000 cm$^{-1}$ to around 1200 cm$^{-1}$. The mid-infrared light source may be tuned to between around 1040 cm$^{-1}$ to around 1180 cm$^{-1}$. The mid-infrared light source may be tuned to between around 1070 cm$^{-1}$ to around 1090 cm$^{-1}$. The sensor may also include a spacer configured to locate the collector element at an optimal distance.

A method for noninvasively measuring in vivo blood glucose concentrations from the skin of a test subject is also disclosed. The method includes irradiating the skin with a mid-infrared light source. The mid-infrared backscattered light is collected from the skin with a collector element. The backscattered light is directed to a detector. The strength of the signal received in a defined region by the detector is compared with a calibration curve for that defined region. The mid-infrared light source may be a quantum cascade laser. Optical fibers may be used to irradiate the skin with the mid-infrared light source. The optical fibers may be hollow core optical fibers. The collector device may include an integrating sphere. The collector element may be a bundle of two or more optical fibers.

The method may also include collecting the mid-infrared backscattered light from the skin with a probe containing or connecting to optical fibers coupled to the mid-infrared light source. The probe may be configured to be placed on the skin of the test subject to take glucose level readings. The mid-infrared light source may be tuned to between around 1000 cm$^{-1}$ to around 1200 cm$^{-1}$. The mid-infrared light source may be tuned to between around 1040 cm$^{-1}$ to around 1180 cm$^{-1}$. The mid-infrared light source may be tuned to between around 1070 cm$^{-1}$ to around 1090 cm$^{-1}$.

DETAILED DESCRIPTION OF THE INVENTION

The mid-infrared (mid-IR) band is promising for the field of noninvasive in vivo glucose detection, as the glucose molecule contains fundamental vibrational resonances between 8-10 μm which are not overlapped by other biological absorbers except water. Water is a broad featureless absorber throughout the near and mid-IR, but its absorption coefficient is roughly four orders of magnitude greater in the mid-IR region than in the near-IR region, which has been the biggest challenge for researchers focusing on noninvasive in vivo glucose detection in the mid-IR regime. However, recent developments in mid-IR light source technology, including pulsed Quantum Cascade (QC) lasers able to provide high peak powers on the order of hundreds of milliwatts while maintaining average powers on the order of a few milliwatts have provided the capacity to obtain more robust signals from skin regions where mid-IR light had previously been considered to be undetectable.

Resonances of the glucose molecule in the mid-infrared range do not share overlapping spectral features to other skin elements, avoiding the requirements for complex multivariate analysis associated with near-IR methods.

Glucose levels in different biological components in skin correlate differently with blood glucose levels, and even the same components in different skin layers provide unique correlations. Interstitial fluid (ISF) in the dermis layer of skin has been shown to provide the best correlation of glucose concentration to blood glucose levels when compared to ISF in other skin layers. The disclosed system can measure physiologically relevant ranges of glucose concentrations in dermal ISF.

Figure 1:
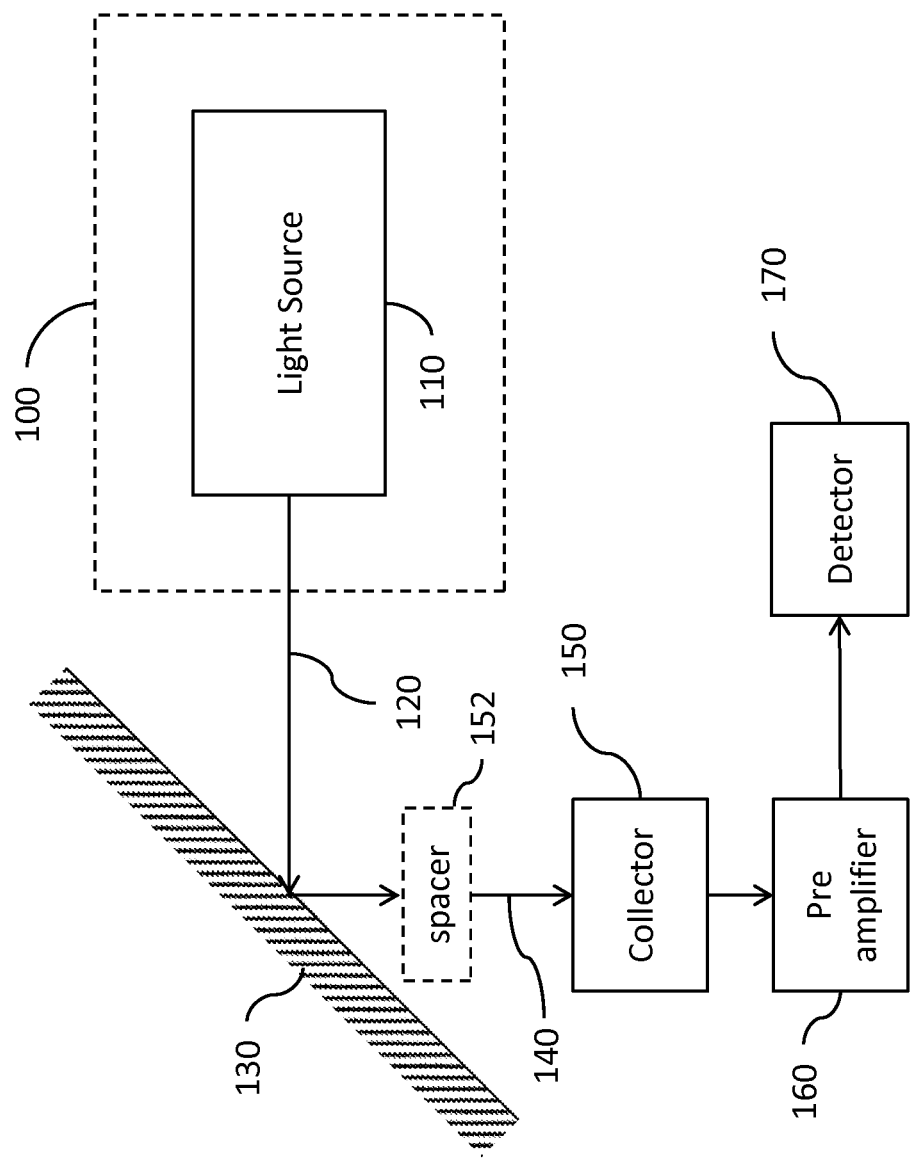
FIG. 1 is an illustration of an embodiment of a mid-infrared glucose detection system.

FIG. 1 discloses a mid-infrared glucose detection system. A Mid-IR light source 110 may be contained in housing 100. The mid-infrared light leaves the light source 110 and may be passed through an optical fiber 120 or set of lenses to direct the light to the target 130, typically human skin. The backscattered light shown generally by reference number 140 reflected from the target 130 is collected by a collector 150. A spacer 152 may optionally be provided to locate the collector 150 at an optimal distance as discussed below. The collected light is then optionally sent to a preamplifier 160 before being directed to detector 170.

Figure 2:
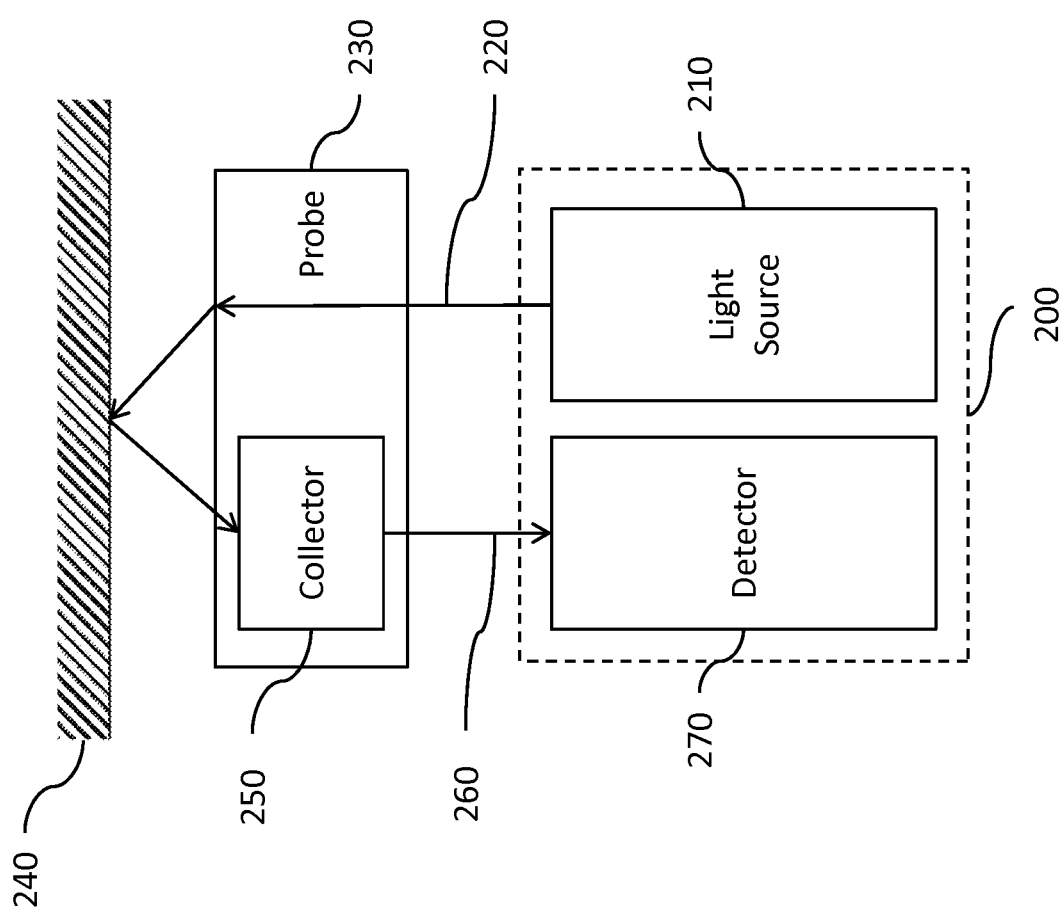
FIG. 2 is an illustration of an additional embodiment of a mid-infrared glucose detection system including a probe.

While the basic system configuration disclosed in FIG. 1 may be appropriate in some instances, a system that includes a probe unit may also be of benefit. A probe generally provides a hand held device configured to allow a user to easily acquire readings from a test subject e.g., the arm or hand. FIG. 2 is a block diagram of a mid-infrared glucose detection system including a probe 230. In this example, housing 200 contains both the Mid-IR light source 210 and the detector 270. The mid-infrared light leaves the light source 210 and is passed through an optical fiber 220, which directs the light to probe 230. The optical fiber 220 may terminate at the probe 230, or may extend through the probe 230, as shown in FIG. 2. After leaving the probe, the light strikes the measurement target 240. The light backscattered by the target is collected by the collector 250 in the probe 230 and is directed into an optical fiber 260. In this example, the light is then directed into the detector 270 without a preamplifier or other component. It should be understood that beam routing fibers and lenses as well as a pre-amplifier may be used in this configuration as well.

The light source is typically tunable. One example of an embodiment of the disclosed system is a mid-infrared light from e.g., broadband mid-infrared Fourier Transform Infrared (FTIR) spectrometers or Quantum Cascade laser sources, typically having a wavenumber range from around 1000 $cm^{-1}$ to around 1200 $cm^{-1}$. To minimize impact on the human body, the average power needs to be kept to a minimal level. In one embodiment, a higher power light source is pulsed on and off in short bursts (typically around 100 ns) with longer delays between each pulse to generate a strong peak signal while maintaining a low average power for example a few milliwatts. The primary driver for this is to generate a sufficiently strong pulse to reach the dermis, and, hence, the ISF in the dermis, without generating such a strong pulse that you're reaching beyond the dermis or causing other problems for either the system or the user.

The collector may be any component that captures the backscattered light, e.g., an integrating sphere, a fiber bundle, or a Winston cone, or a combination of components. Although not required, ideally the collector would be placed in a position that allows the measurement of the highest signal possible backscattered from the target.

The optimal location for capturing the backscattered light is partially dependent on the light source. A broadband FTIR may have a broad maximum centered on the specular angle, while a QC laser may not. For example, in one system configuration, at 1120 $cm^{-1}$, a broadband FTIR light source had a broad maximum, with a half width half maximum of 32 degrees, centered on the specular reflection angle. However, in a comparable system with a QC laser, a narrow maximum was found to be centered approximately 30 degrees away from the specular angle. Although backscattered light may be gathered by the collector, the system may also require a series of amplifiers or preamplifiers in order to provide the highest quality optical signal to the detector.

Figure 3:
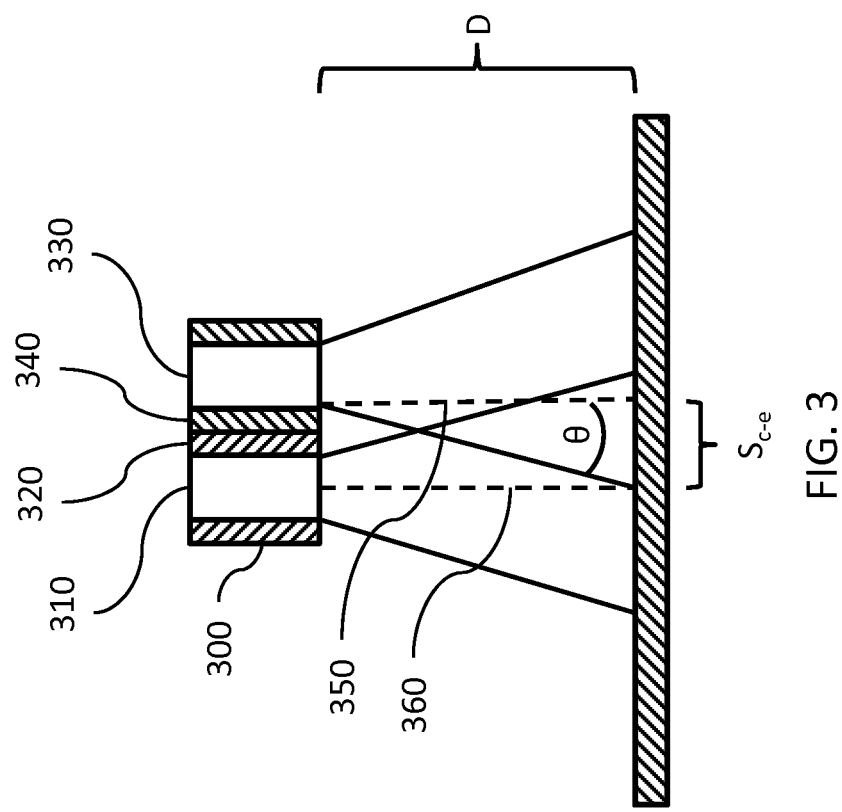
FIG. 3 is an illustration of target and sensor geometry for collecting optimal signal.

Depending on the configuration, there may also be an optimal distance from the target to the collection point. The optimal distance maximizes the crossover between the illumination and collection area as well as the signal magnitude. At zero distance, the signal is maximized but there is no crossover; at infinite distance, crossover is maximized but there is no signal. FIG. 3 illustrates one example of an optimal distance. Probe 300 contains a light emitting fiber 310 with cladding 320, and a light collection fiber 330 with cladding 340. The distance between the outer edge 350 of the collection fiber 330 and the centerline 360 of the emitting fiber 310 is indicated by $S_{c-e}$. In this example, this is the radius of the emitting fiber 310 plus the thickness of cladding 320 plus the thickness of cladding 340. Typically, an estimation for the optimal distance D from the target to the collector can then calculated by dividing $S_{c-e}$ by the tangent of the acceptance angle θ. For example, in one configuration with a single emitting fiber and a single collecting fiber had a $S_{c-e}$ value of 0.614 mm, and an acceptance angle of 6°. Thus the estimation for optimal distance was 5.842 mm. As the target with these sensors is not located on the surface of the skin, but rather inside the dermis, the optimal distance is somewhat less. In practice, this single emitting fiber and single collecting fiber configuration had an optimal distance of approximately 5 mm. It should be understood that a spacer, may optionally be provided to locate the collecting fiber at the optimal distance, see e.g., reference number 152 in FIG. 1.

Additionally, depending on the system, thermally-induced noise in the detector may lower the signal-to-noise ratio to unacceptable or unusable levels. In such cases, a detector with a cooling system may be required. Typically, this may involve cryogenic fluids such as liquid nitrogen or liquid helium. For example, in a system with a FTIR spectrometer which emits incoherent broadband (650-4000 $cm^{-1}$) continuous wave light with an integrated power of 7 mW, a liquid nitrogen cooled mercury cadmium telluride (MCT) detector was used to collect the transmitted light. Alternate methods of cooling, such as devices utilizing thermoelectric cooling, may be adequate as well.

Once sufficient signal is detected, absorption features should be found that allow different glucose levels to be identified or otherwise differentiated. Ideally, certain wavenumber regions showing desirable absorption features that may be of benefit should be identified. As an example, typical embodiments of the disclosed system show a clear increase in the width and depth of the absorption feature in the region around 1070 $cm^{-1}$ when glucose levels are increased. Therefore, it would be advantageous to tune the mid-infrared light source to a wavenumber in that region, or any other regions with similar desirable features. While a single region of interest may be sufficient, additional regions are beneficial, and generally, those regions are not contiguous. For example, while one region may be from 1070-1090 cm$^{-1}$, another region may be from 1120-1140 cm$^{-1}$, and a third region may be from 1155-1175 cm$^{-1}$. Accordingly, the system may be configured to generate Mid-IR and collect back scattered light in several regions of interest and to combine the signals from each region of interest.

When features are identified that allow differentiation between glucose levels, the system can be calibrated. Predictions can be made utilizing any appropriate technique. For example, chemo-metric prediction of principle component concentrations in a given dataset usually employs partial least squares regression (PLSR). PLSR is a technique that combines linear regression with principle component analysis, and it is optimal for situations where linearly correlated quantities are measured, such as absorbance versus concentration for this specific scenario. However, other approaches may be valid as well. For example, prediction analysis can also be conducted using linear regression of spectral integrals taken around the prominent glucose absorption feature at 1080 cm$^{-1}$, spanning from 1075-1085 cm$^{-1}$. By utilizing integration within that region, the breadth and depth of the glucose absorption in a dense medium like ISF could be better resolved. In one configuration, integral regression performed slightly more favorably than PLSR—which tended to slightly overshoot predictions—yielding a 4% smaller aggregate average error.

To begin building a calibration matrix, one option is to utilize in vitro results. In vitro transmission spectra of glucose solution samples may be acquired in the following manner: light from a mid-IR source is transmitted through a 100 μm path length pressure sealed liquid cell containing a solution. Solutions containing different glucose concentrations may be created from 10% (equivalent to a 10,000 mg/dL concentration) glucose solution obtained from e.g., TekNova, which may be serially diluted with the background material (water, serum, or Intralipid) to create concentrations ranging from 1 mg/dL to 10,000 mg/dL. Serum may be obtained from e.g., Animal Technologies, Inc., while Intralipid may be obtained from e.g., Sigma Aldrich. Spectra may be acquired using software that is interfaced to the source. The spectrum collected for each run may result from the averaging of multiple voltage readings from the detector's preamplifier collected for each wavenumber. Calibration and prediction using transmitted mid-IR spectra of concentrations too high to be physiologically relevant (500, 1000, 5000, and 10000 mg/dL) and concentrations of 1, 5, 10, 50, and 100 mg/dL may be done. When prediction spectra were analyzed with the complete calibration vector, a nearly 1:1 linear relationship between predicted concentrations and expected concentrations; $R^2$ values of 0.999 (water—FIG. 1b), 1.00 (serum—FIG. 1c), and 1.00 (Intralipid—FIG. 1d) were obtained. However, when using only concentrations up to 100 mg/dL for calibration and prediction, $R^2$ values deviated by up to 10%, showing that the near-perfect linear relationship stemmed from the overwhelming signal to noise ratio of the absorption features of the higher concentrations. The accuracy in the data was extracted via plotting the predicted concentration versus the expected concentration on a Clarke error grid. For aqueous glucose solutions, average values of predictions were clinically accurate throughout the entire 1-400 mg/dL region, and accurate and practical (non-negative) concentration values for solutions containing as low as 20 mg/dL concentrations of glucose were obtained. For serum solutions, slightly smaller standard deviations for 150 and 200 mg/dL, and slightly larger deviations for concentrations under 50 mg/dL (hypoglycemic range) were obtained, with a cutoff at 30 mg/dL, below which we do not always obtain non-negative prediction concentrations.

As one alternative, however, in vivo calibration curves can also be utilized. For example, calibration can be done via comparison of measured spectra with e.g., a commercial electrochemical (finger prick) glucose meter for a limited number of readings. Starting from a point of low blood sugar, consuming jellybeans and taking measurements as the blood sugar rises may be an appropriate technique for building a calibration matrix for a given individual.

It should be understood that many variations are possible based on the disclosure herein. Although features and elements are described above in particular combinations, each feature or element can be used alone without the other features and elements or in various combinations with or without other features and elements.

What is claimed is:

1. A noninvasive mid-infrared in vivo glucose sensor for use in connection with interstitial fluid in the skin of a test subject, the sensor comprising:
    a mid-infrared light source configured to deliver a light beam to the skin of the test subject, the mid-infrared light source capable of being tuned to between around 1000 cm$^{-1}$ to around 1200 cm$^{-1}$; and
    a collector element configured to collect light having a plurality of wavelengths from the skin and direct all of the collected light to an optical detector element without passing through a filter, the optical detector element configured to measure the collected light from the skin at the plurality of wavelengths.

2. A sensor according to claim 1, wherein the mid-infrared light source is a quantum cascade laser.

3. A sensor according to claim 1, further comprising optical fibers configured to deliver the light beam to the skin of the test subject.

4. A sensor according to claim 3, wherein the optical fibers are hollow core optical fibers.

5. A sensor according to claim 1, wherein the collector element is an integrating sphere.

6. A sensor according to claim 1, wherein the collector element is a bundle of two or more optical fibers.

7. A sensor according to claim 1, further comprising:
    a probe containing or connecting to optical fibers coupled to the mid-infrared light source;
    wherein the probe is configured to be placed on the skin of the test subject to take glucose level readings.

8. A sensor according to claim 1, wherein the mid-infrared light source is tuned to between around 1040 cm$^{-1}$ to around 1180 cm$^{-1}$.

9. A sensor according to claim 1, wherein the mid-infrared light source is tuned to between around 1070 cm$^{-1}$ to around 1090 cm$^{-1}$.

10. A sensor according to claim 1, further comprising a spacer configured to locate the collector element at an optimal distance.

11. A noninvasive mid-infrared in vivo glucose sensor for use in connection with interstitial fluid in the skin of a test subject, the sensor comprising:
    a mid-infrared light source configured to deliver a light beam to the skin of the test subject, the mid-infrared light source capable of being tuned to between around 1000 cm$^{-1}$ to around 1200 cm$^{-1}$; and
    a collector element configured to collect light having a plurality of wavelengths from the skin and direct all of the collected light to an optical detector element configured to measure the collected light from the skin at the plurality of wavelengths, wherein the mid-infrared light source is configured to provide a peak power greater than 100 milliwatts and an average power of less than 10 milliwatts.

* * * * *